(12) United States Patent
Hong et al.

(10) Patent No.: US 8,759,545 B2
(45) Date of Patent: Jun. 24, 2014

(54) METHOD OF PREPARING LACTIDE FROM LACTATE

(75) Inventors: Chae Hwan Hong, Gyeonggi-do (KR); Si Hwan Kim, Gyeonggi-do (KR); Jiyoun Seo, Gyeonggi-do (KR); Do Suck Han, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 13/600,724

(22) Filed: Aug. 31, 2012

(65) Prior Publication Data

US 2013/0267716 A1 Oct. 10, 2013

(30) Foreign Application Priority Data

Apr. 4, 2012 (KR) .................. 10-2012-0034860

(51) Int. Cl.
*C07D 319/00* (2006.01)
(52) U.S. Cl.
USPC ........................................................ 549/274
(58) Field of Classification Search
USPC ........................................................ 549/274
See application file for complete search history.

(56) References Cited

U.S. PATENT DOCUMENTS 5,319,107 A * 6/1994 Benecke et al. .............. 549/274

FOREIGN PATENT DOCUMENTS

| JP | 06065230 A | 3/1994 |
| JP | 11035579 A | 2/1999 |
| JP | 2002300898 A | 10/2002 |
| JP | 2004149418 A | 5/2004 |
| KR | 10-2008-0018650 | 2/2008 |
| KR | 10-2008-0018657 | 2/2008 |
| KR | 10-2012-0009879 | 2/2012 |

* cited by examiner

*Primary Examiner* — Taylor Victor Oh
(74) *Attorney, Agent, or Firm* — Edwards Wildman Palmer LLP; Peter F. Corless

(57) ABSTRACT

The present invention provides a method of preparing lactide with a high yield from lactate obtained through a fermentation process. In certain embodiments, the invention provides a method of preparing high-purity lactide with a high yield, wherein the method comprises treating lactate with a specific solvent, using a catalyst, and phase-separating the resultant. In accordance with the invention, costs for manufacturing polylactic acid can be considerably reduced.

9 Claims, 2 Drawing Sheets

METHOD OF PREPARING LACTIDE FROM LACTATE

CROSS-REFERENCE TO RELATED APPLICATION

This application claims under 35 U.S.C. §119(a) the benefit of Korean Patent Application No. 10-2012-0034860 filed Apr. 4, 2012, the entire contents of which are incorporated herein by reference.

BACKGROUND (a) Technical Field

The present invention provides a method of preparing lactide with a high yield from lactate, which are obtained through fermentation.

(b) Background Art

Since the 20th century, rapid global industrialization has caused the global economy largely dependent upon fossil fuel resources, particularly, petroleum resources. It has been noted that consumption of petroleum resources has been considerably increased along with the rapid development of industries and global population growth. However, petroleum is not a recyclable resource, and its reserves are limited. In addition, the carbon dioxide emission from the consumption of fossil fuels has been blamed as a main cause for global warming. It has been the focus of researches in the related industries to improve the efficiency of the petroleum economy, and to reduce the carbon dioxide emission.

Recently, plant-derived (i.e., biomass) polymers have received public attention due to their eco-friendliness, particularly, with reduced carbon dioxide emissions (rather than biodegradability). The biomass polymers are produced from recyclable plant resources (such as, corns, beans, sugar canes, and woods) by using chemical or biological methods. Among the biomass polymers, polylactic acid, a linear aliphatic polyester, is a carbon neutral and eco-friendly thermoplastic polymer. Polylactic acid is produced by polymerizing monosaccharides obtained by starch-fermenting corns and potatoes, or produced by saccharifying and fermenting plant-derived cellulose.

Despite various advantages that polylactic acid offers, polylactic acid however has not been considered to be suitable to be used in vehicles, due to its expensive manufacturing costs compared with petrochemical-derived polymers. In addition, industrial applications of polylactic acid resins are limited due to their poor physical properties. To be used in automotive chassis and engines, polylactic acid resins need to be modified to have improved physical properties, such as, a high thermal resistance and an impact strength.

To achieve these goals, there is a known technique of preparing stereo-complex type resins in the art. The technique involves blending enantiomer resins. To develop this technique, L-polylactic acid and D-polylactic acid need to be manufactured in an economical manner. Specifically, in the preparation of polylactic acid, resins are manufactured a process comprising steps of converting fermented and purified lactic acid into lactide, and a ring-opening polymerization of the lactide. In this process, there is a need to economically improve the step of converting lactic acid to lactide.

Further, during the fermentation step, the lactic acid that is used to prepare polylactic acid exists in a salt form, for example, ammonium lactate ($NH_4^+Lac^-$) and sodium lactate ($Na^+ Lac^-$). This occurs because a base is added during the fermentation step to adjust acidity. Accordingly, a process of manufacturing lactic acid comprises concentrating lactate in the form of a salt and converting the concentrated lactate in the form of a salt to obtain pure lactic acid. Clearly, the manufacturing costs are increased due to cost associated with the preparation of pure lactic acid. Therefore, if lactide can be produced from lactate instead of from pure lactic acid, the manufacturing cost of lactide would be reduced. However, up to today, such a process with an optimized technique has not yet been developed to achieve a satisfactory level.

In the art, solid-phase lactide is generally prepared from liquid-phase lactic acid that is obtained through fermentation, purification, and concentration processes. Accordingly, there is a need to develop a process or catalyst thereof that may be used to economically prepare lactide from liquid-phase lactic acid.

So far, the majority of the methods for manufacturing lactide comprise polymerizing low molecular weight polylactic acid obtained through fermentation, purification, and concentration, and depolymerizing the low molecular weight polylactic acid at a high temperature, so that cyclo lactide is prepared by back biting in low molecular weight polylactic acid chains.

For example, Korean Patent Application Publication No. 2008-18657 discloses a method of preparing lactide for synthesizing L-lactic acid from L-, D-, or DL-lactic acid, the method comprising the steps of: (1) synthesizing low molecular weight lactic acid from lactic acid; and (2) preparing crude lactide by heating and pressing the low molecular weight lactic acid synthesized in the step (1) in the presence of a catalyst, wherein the catalyst is a metal oxide catalyst including a metal selected from the group consisting of Sn, Zn, Fe, and Sb.

Korean Patent Application Publication No. 2008-18650 discloses a method of isolating chirally pure D- and L-lactides. The method includes: synthesizing low molecular weight lactic acid from lactic acid; preparing crude lactide from the low molecular weight lactic acid in the presence of a catalyst; adding the crude lactide to a solvent to obtain a solution of the crude lactide; stirring the solution at a constant temperature; centrifuging the stirred solution; and drying the centrifuged sample.

Korean Patent No. 171431 discloses a method of preparing lactide from an aqueous lactic acid feed, particularly, with an enriched L1A, L2A, L3A, or a mixture thereof. The method comprise the steps of: (a) converting an aqueous lactic acid feed to its vapor phase by evaporating the lactic acid feed in a hot gas stream; (b) passing the feed vapors through a vapor phase reaction zone maintained at elevated temperature; and (c) withdrawing from the reaction zone lactide, water, and unreacted aqueous lactic acid feed.

Further, Japanese Patent Application Publication No. 1995-165753 discloses a method of purifying lactide by removing meso-lactide from a mixture of L-lactide and/or D-lactide, and mesolactide. The method includes a step of bringing the mixture into contact with water. Moreover, Japanese Patent Application Publication No. 2004-149418 discloses a method of purifying lactide through steps including bringing a solidified crude lactide into contact with water, separating the solidified crude lactide into an aqueous phase and a solid phase, and recovering the solid phase.

In general, these methods are performed by preparing low molecular weight polylactic acid, and then performing pyrolysis to prepare lactide. Since a heat treatment at a high temperature (i.e., greater than 230° C.) is performed and gaseous lactide is collected by using low temperature trap, the processes are complex and uneconomical.

U.S. Pat. No. 5,750,732 discloses a method of producing a cyclo ester by mixing lactic acid, an organic solvent (such as, xylene), and a catalyst (such as, sulfonic acid) to obtain a mixture, and heating and refluxing the mixture to prepare lactide. Japanese Patent Application Publication No. 1994-0031175 discloses a catalyst useful for preparing lactide having low hygroscopicity in a high yield. The preparation involves using lactic acid prepolymer or lactic ester and a catalyst without a high temperature heat treatment. European Patent Nos. 261,572 and 275,581 disclose another type of catalysts, such as, tin powder, tin halide, and tin carboxylate. Moreover, UK Patent No. 1,007,347 discloses the use of tin alkoxide as a catalyst. Korean Patent No. 2010-5820 discloses a method of synthesizing chirally pure lactide. The method includes: (A) dissolving lactic acid or alkyl lactate in an organic solvent; (B) adding an enzyme to the organic solution of the lactic acid or alkyl lactate and stirring for 4 to 24 hours; and (C) separating chirally pure lactide.

However, these existing techniques in the field are not economical s as they are generally complicated or have low yields.

SUMMARY OF THE DISCLOSURE

To solve the above-noted problems, the present inventors found unexpectedly that lactide can be manufactured with a high yield through performing a catalytic reaction on lactate, with steps including adding a specific solvent and phase-separating the resultant.

Thus, the present invention provides a simple method of manufacturing lactide. The method comprises performing a catalytic reaction on lactate in the presence of an organic solvent, and phase-separating the resultant.

The present invention also provides an economical method of manufacturing high-purity lactide with a high yield.

In an aspect, the present invention provides a method of preparing lactide including: (a) converting an aqueous lactate solution into lactide via a catalytic reaction in the presence of a first organic solvent suitable for an azeotropic distillation with water; (b) phase-separating the converted product obtained in the step (a) using a mixture of a second organic solvent and water; and (c) obtaining lactide by extracting an organic phase separated in the step (b) followed by evaporating the solvent.

Advantageous Effects

According to the method of the present invention, high-purity lactide can be manufactured with a high yield through a catalytic reaction of lactate in the presence of an organic solvent followed by phase-separating the resultant. The manufacturing process is simple and economical, since a high temperature treatment is not required, and a recovery rate of lactide may be increased by the phase-separation.

Furthermore, lactide prepared according to the present invention can be used to prepare polylactic acid. By replacing conventional petroleum-derived polypropylene-based materials and polycarbonate materials with the biomass-derived material as materials to construct interior and exterior parts of vehicles, the dependency of petrochemical-derived compounds can be reduced, and the manufacturing costs for vehicles can be considerably reduced.

BRIEF DESCRIPTION OF THE DRAWINGS

The above and other features of the present invention are described in detail with reference to certain exemplary embodiments thereof. Further, accompanying drawings are given herein below by way of illustration only, and should not be construed as limitative of the present invention.

Figure 1:
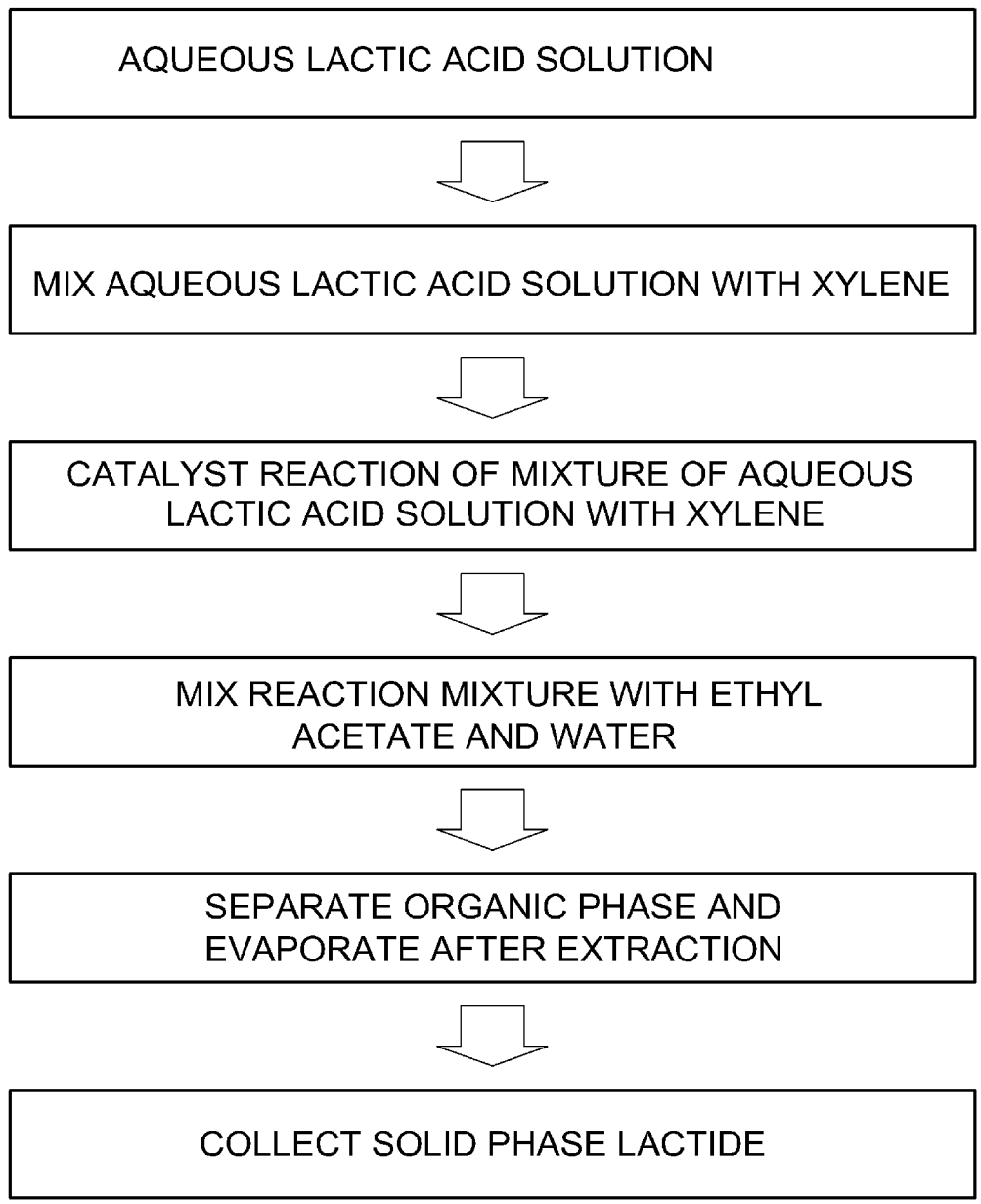
FIG. 1 is a scheme showing a preparation method according to the present invention, particularly, a process of preparing solid-phase lactide from a D-lactic acid fermented broth.

It should be understood that the drawings are not necessarily to scale, presenting a simplified representation of various features illustrative of the basic principles of the invention. The specific features of the present invention as disclosed herein, including, for example, specific dimensions, orientations, locations, and shapes, can be determined in part by a particular intended application and use environment.

In the figures, reference numbers refer to the same or equivalent parts of the present invention throughout the several figures of the drawing.

DETAILED DESCRIPTION

Hereinafter reference is made in detail to various embodiments of the present invention, and examples that are illustrated in the accompanying drawings and described below. While the invention is described in conjunction with exemplary embodiments, it should be understood that the description provided herein is not intended to limit the invention to those exemplary embodiments. On the contrary, the invention is intended to cover not only the exemplary embodiments, but also various alternatives, modifications, equivalents and other embodiments. Such equivalents are considered to be within the scope of this invention and are covered by the claims provided below.

As lactic acid has one asymmetric carbon atom, it may be obtained in two enantiomeric forms of lactic acid. On the other hand, lactide has two asymmetric carbon atoms. It follows that lactide may be obtained in three stereoisomeric forms: L-lactide in which both asymmetric carbon atoms possess the L (or S) configuration; D-lactide in which both asymmetric carbon atoms possess the D (or R) configuration; and meso-lactide in which one asymmetric carbon atom has the L-configuration and the other has the D-configuration. L-lactide and D-lactide are enantiomers. In the production of lactide from lactic acid, it would be advantageous if the absolute configuration of the lactic acid feed is maintained after it is converted to lactide.

As fermented products, aqueous lactate typically used in the method of the present invention exists in the form of ammonium lactate ($NH_4^+Lac^-$) or sodium lactate ($Na^+Lac^-$) in water. These forms are obtained by concentrating lactate in a desalting process, and may be produced when lactic acid monomers are converted into dimers or trimers during purification and concentration processes.

Here, the terms are defined as follows.

L1A salt: lactate, or lactic acid monomer, or 2-hydroxypropionic acid salt ($NH_4^+Lac^-$ or $Na^+$ $Lac^-$)

LD: lactide, or 3,6-dimethyl-1,4-dioxane-2,5-dione (cyclic structure)

L2A: lactoyllactic acid, or linear lactic acid dimer

L3A: lactoyllactoyllactic acid, or linear lactic acid trimer

The present invention provides an efficient method of preparing lactide from lactate. The properties of lactic acid are described above.

Lactate in an aqueous solution is converted to lactide by an acid catalytic reaction in the presence of a first organic solvent that is suitable for an azeotropic distillation with water. Lactic acid used herein is obtained from a lactic acid feed through fermentation. The lactic acid is an aqueous lactate solution including 10 to 98% of lactic acid.

The aqueous lactate solution is mixed with a first organic solvent that is suitable for an azeotropic distillation with water. Here, the first organic solvent may be an organic solvent selected from the group consisting of benzene, toluene, and xylene. According to the present invention, the first organic solvent is used to efficiently induce generation and separation of lactide. The amount of the first organic solvent may be adjusted such that a weight ratio of lactic acid/first organic solvent is in the range of 0.1 to 0.9. If the weight ratio of lactic acid/first organic solvent is less than 0.1, the amount of lactide decreases due to a relatively small amount of the lactate solution. Accordingly, the economical efficiency of the method is decreased. On the other hand, if the weight ratio of lactic acid/first organic solvent is greater than 0.9, the catalytic reaction takes a longer time to complete due to a relatively large amount of water contained in the lactate solution.

The conversion of lactic acid to lactide is carried out via a catalytic reaction wherein the catalyst is added to the mixture of the aqueous lactate solution and the first organic solvent. In this regard, the catalyst may include one selected from the group consisting of HCl, $H_2SO_4$, acetic acid, sulfonic acid-based catalyst (p-TsOH, CSA, or the like), Zn, ZnO, $ZnX_n$, $SnX_n$, $InX_n$, $Ln(OTf)_3$, $Sc(OTf)_3$, $Yb(OTf)_3$, Zeolite, Amberlyst, Amberlite, and Dowex, or a mixture of at least two thereof. In certain embodiments, the catalyst is Zn, ZnO, $ZnCl_2$, $SnCl_2$, $SnCl_4$, Zeolite, $Sc(OTf)_3$, or $Yb(OTf)_3$. The amount of the catalyst may be adjusted such that a molar ratio thereof is 0.1 to 10 mol % with respect to lactic acid.

After the catalyst is added, reaction may be performed at a temperature in the range of 50 to 200° C. at an atmospheric pressure or in a reduced pressure. In certain embodiments, the reaction temperature is in the range of 100 to 200° C. If the reaction temperature is too low, reactivity of the catalyst decreases, thereby rendering the reaction not practical. On the other hand, if the reaction temperature is too high, the lactate solution is discolored due to excessive heat, thereby deteriorating physical properties of products.

Water vapor is generated as the reaction between the mixture solution and the catalyst proceeds. The water vapor may be removed by using, for example, a condenser.

The converted lactide in a liquid-phase is then phase-separated by using a mixture of a second organic solvent and water.

That is, the obtained liquid-phase lactide is transferred to a secondary reactor, which is separated into an organic phase and water. The second organic solvent used for the phase separation may be selected from the group consisting of ethyl acetate, ether, methylene chloride, chloroform, and hexane. In certain embodiments, the second organic solvent is ethyl acetate or ether. The amount of the second organic solvent may be adjusted so that a weight ratio of water/second organic solvent is in the range of 0.1 to 0.9. When the second organic solvent and water are mixed with the lactide, lactide moves to an upper layer of the organic phase, which can be separated from water in a lower layer.

Then, the separated organic phase is subjected to an extraction. The solvent is removed therefrom to obtain lactide.

In this step, once the upper layer (that is, the organic phase including lactide) is extracted, and the solvent is evaporated, lactide in a solid-phase may be obtained with a high yield.

According to the present invention, lactide is prepared through a fine chemical reaction technique including adding a Lewis-acid catalyst to a liquid-phase of a mixture of lactate and a solvent. Specifically, the first organic solvent, lactate in a liquid-phase, and a catalyst are added to a primary reactor, the reactor is then heated, and a gaseous moisture is discharged afterwards, with the first organic solvent dominantly remaining in the reactor. Under these conditions, a catalytic reaction on the lactate in the presence of the catalyst occurs, thereby producing lactide. Then, the liquid-phase mixture containing first organic solvent and lactide is transferred to a secondary reactor, where it is subjected to an extraction using a mixture of water and the second organic solvent. During the extraction, lactide moves to the upper layer (i.e., the organic phase). The solvent in the liquid phase is then evaporated from the solvent-lactide mixture, which is subsequently transferred to a tertiary reactor to prepare lactide in solid-phase.

In the secondary reactor, lactic acid and low molecular weight polylactic acid as impurities move to the lower layer (that is, the water layer) during the extraction process, thereby increasing the purity of lactide.

Figure 2:
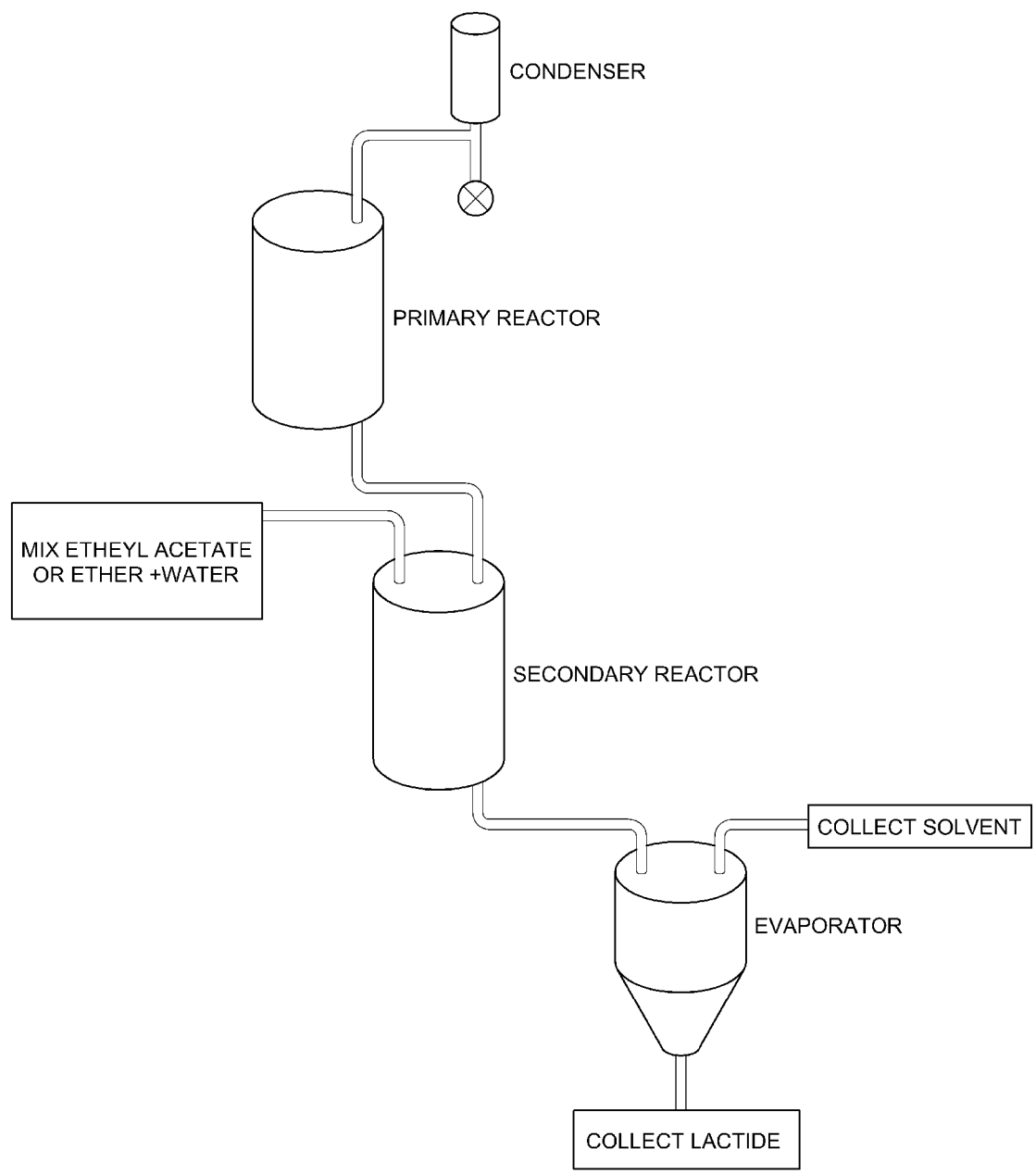
FIG. 2 illustrates a device that may be used in a process of preparing lactide from lactate, including separating impurities and recovering desired products.

The preparation process according to the present invention is illustrated in FIG. 1. FIG. 2 shows an example of a device that may be used in accordance with the invention. Specifically, FIG. 1 schematically shows a process of preparing lactide from D-lactic acid fermented broth and polylactic acid, and FIG. 2 shows a process of preparing lactide from lactate and separating lactide from impurities.

According to the present invention, if L-lactate is used as a starting material, L-lactide will be prepared. If D-lactate is used as a starting material, D-lactide will be prepared. Thus, the technique of the invention can have a wider application. Lactide can be used to prepare polylactic acid, a biomass-derived material. And polylactic acid may replace conventional petroleum-based polypropylene materials and polycarbonate materials as, for example, interior/exterior materials of vehicles. Consequently, the dependency of petrochemicals derived compounds may be reduced. The manufacturing costs for interior and exterior materials of automotive parts may be considerably reduced as well.

According to the present invention, since the catalytic reaction of the aqueous lactate is carried out at atmospheric pressure, energy as required thereof decreases. In addition, since lactide is recovered in a high purity, the method is economical and environment-friendly.

Further, asymmetric carbon atom in the produced lactide mainly has the same absolute configuration as that in the aqueous lactate of the lactic acid feed.

In addition, unreacted aqueous lactate may be recycled. Furthermore, lactide may be prepared by using a device commonly used in the art. However, manufacturing costs for preparing gaseous lactide will be higher since the process requires a cyclone operating at a low temperature and a low temperature cooling device.

The invention is described herein in detail with reference to preferred embodiments thereof. However, it should be appreciated by those skilled in the art that changes may be made in these embodiments without departing from the principles and spirit of the invention, and within the scope of the appended claims and their equivalents. Unless otherwise defined, all % and ratios are based on weight, and all units are based on the metric system. All examples used herein are incorporated herein in their entireties by reference.

EXAMPLES

The following examples illustrate the invention and are not intended to limit the same.

Example 1

A 100 mL round-bottom flask, a dean stark, and a cooling pipe were used. The dean stark is disposed at the center for an azeotropic distillation, and the cooling pipe is connected to an upper portion of the dean stark.

To the round-bottom flask, 100 mg (1.1101 mmol) of ammonium lactate and 40 mL of xylene were added to obtain a mixture. Subsequently, 6.88 mg (0.0111 mmol) of ytterbium triplate was added to the mixture as a catalyst. The mixture was stirred. The flask was heated using a heating plate for 14 hours, and then lactate, lactide produced by the catalytic reaction, lactate by the azeotropic distillation, and other by-products were transferred to a separation funnel with the solvent (xylene). The amount of the catalyst, ytterbium triplate (Yb(OTf)$_3$), was about 1 mol %.

The solvent, lactide, and impurities obtained from the separation funnel were mixed with ethyl acetate and water to separate the impurities. 40 mL of ethyl acetate and 40 mL of water were added thereto based on the total volume of the solvent, lactide, and impurities. The ethyl acetate layer was subjected to an extraction and the extract was transferred to a rotary evaporator. The ethyl acetate and the solvent (xylene) were evaporated to obtain 58.4 mg (0.4052 mmol) of lactide (73%). $^1$H NMR (400 MHz, CDCl$_3$) δ 5.03 (q, 2H), δ 1.68 (d, 6H), $^{13}$C NMR (100 mHz) δ 167.4, δ 72.5, δ 15.8, mp 97° C.

Comparative Example 1

A 100 mL round-bottom flask, a dean stark, and a cooling pipe were used. The dean stark is disposed at the center for azeotropic distillation, and the cooling pipe is connected to an upper portion of the dean stark.

To the round-bottom flask, 100 mg (1.1101 mmol) of ammonium lactate and 40 mL of xylene were added to obtain a mixture. The mixture was stirred without using a catalyst. The flask was heated using a heating plate for 14 hours, and then ammonium lactate, lactide produced by azeotropic distillation and other by-products were transferred to a separation funnel with the solvent (xylene).

The solvent, lactide, and impurities obtained from the separation funnel were mixed with ethyl acetate and water to separate the impurities. 40 mL of ethyl acetate and 40 mL of water were added thereto based on the total volume of the solvent, lactide, and impurities. The ethyl acetate layer was subjected to an extraction and the extract was transferred to a rotary evaporator. The ethyl acetate and the solvent (xylene) were evaporated to obtain 22.5 mg (0.1561 mmol) of lactide (28%).

Comparative Example 2

A 100 mL round-bottom flask, a dean stark, and a cooling pipe were used. The dean stark is disposed at the center for azeotropic distillation, and the cooling pipe is connected to an upper portion of the dean stark.

100 mg (1.1101 mmol) of ammonium lactate and 40 mL of xylene were added to the round-bottom flask to obtain a mixture 2.1 mg (0.0111 mmol) of zinc oxide, as a catalyst, was added to the mixture. The mixture was stirred. The flask was heated using a heating plate for 14 hours, and then lactate, lactide produced by catalyst reaction of lactate by azeotropic distillation and other by-products were transferred to a separation funnel with the solvent (xylene). The amount of the catalyst, zinc oxide (SnCl$_2$) was about 1 mol %.

The solvent, lactide, and impurities obtained from the separation funnel were mixed with ethyl acetate and water to separate the impurities. 40 mL of ethyl acetate and 40 mL of water were added thereto based on the total volume of the solvent, lactide, and impurities. The ethyl acetate layer was subjected to extraction and the extract was transferred to a rotary evaporator. The ethyl acetate and the solvent (xylene) were evaporated to obtain 42.8 mg (0.2970 mmol) of lactide (54%).

Comparative Example 3

A 100 mL round-bottom flask, a dean stark, and a cooling pipe were used. The dean stark is disposed at the center for azeotropic distillation, and the cooling pipe is connected to an upper portion of the dean stark.

100 mg (1.1101 mmol) of ammonium lactate and 40 mL of xylene were added to the round-bottom flask to obtain a mixture. 1 mg (0.0111 mmol) of zeolite, as a catalyst, was added to the mixture. The mixture was stirred. The flask was heated using a heating plate for 14 hours, and then ammonium lactate, lactide produced by the catalytic reaction of ammonium lactate by an azeotropic distillation and other by-products were transferred to a separation funnel with the solvent (xylene). The amount of the catalyst, zeolite was about 1 mol %.

The solvent, lactide, and impurities obtained from the separation funnel were mixed with ethyl acetate and water to separate the impurities. 40 mL of ethyl acetate and 40 mL of water were added thereto based on the total volume of the solvent, lactide, and impurities. The ethyl acetate layer was subjected to extraction and the extract was transferred to a rotary evaporator. The ethyl acetate and the solvent (xylene) were evaporated to obtain 33.5 mg (0.2324 mmol) of lactide (42%).

EXPERIMENTAL RESULTS

Purity and yield of lactides prepared in Example 1 and Comparative Examples 1 to 3 were measured and provided in Table 1 below.

TABLE 1

|  | Example 1 | Comparative Example 1 | Comparative Example 2 | Comparative Example 3 |
|---|---|---|---|---|
| Type of catalyst | Yb(OTf)$_3$ | — | SnCl$_2$ | Zeolite |
| Catalyst (%) | 1.0 mol | 1.0 mol | 1.0 mol | 1.0 wt |
| Temperature (° C.) | 180 | 180 | 180 | 180 |
| Separation using (organic material + water) | YES | YES | YES | YES |
| Yield of lactide (%) | 73 | 28 | 54 | 42 |
| Purity of lactide | >99% | >99% | >99% | >99% |

Referring to Table 1, the yield of lactide from lactate was the highest when the ytterbium triplate was used as the catalyst, the reaction temperature was 180° C., and water was used in the process.

According to the method according to the present invention, a reasonably low cost that is required for replacing petrochemicals derived materials with biomass derived materials may be achieved Polylactic acid may be prepared in a cost effective manner despite the recent trend of increasing oil price.

The invention is described in detail with reference to the embodiments thereof. However, it will be appreciated by those skilled in the art that changes may be made in these embodiments without departing from the principles and spirit of the invention, the scope of which is defined in the appended claims and their equivalents.

What is claimed is:

1. A method of preparing lactide, the method comprising:
   (a) converting an aqueous lactate solution into lactide via a catalytic reaction in the presence of a first organic solvent suitable for an azeotropic distillation with water;
   (b) phase-separating the converted product obtained in the step (a) using a mixture of a second organic solvent and water; and
   (c) obtaining lactide by extracting an organic phase obtained in the step (b) followed by evaporating the solvent.

2. The method of claim 1, wherein lactic acid is present in the aqueous lactate solution at a concentration in the range of 10 to 98% by weight.

3. The method of claim 1, wherein the first organic solvent is selected from the group consisting of benzene, toluene, and xylene.

4. The method of claim 1, wherein the amount of the first organic solvent is adjusted so that a weight ratio of lactic acid to the first organic solvent is in the range of 0.1 to 0.9.

5. The method of claim 1, wherein the catalyst comprises one selected from the group consisting of HCl, $H_2SO_4$, acetic acid, sulfonic acid-based acid catalyst, Zn, ZnO, ZnXn, SnXn, InXn, $Ln(OTf)_3$, $Sc(OTf)_3$, $Yb(OTf)_3$, Zeolite, Amberlyst, Amberlite, and Dowex, and a mixture of at least two thereof.

6. The method of claim 1, wherein the catalytic reaction is conducted at a temperature in the range of 50 to 200° C. at an atmospheric pressure or in a reduced pressure.

7. The method of claim 1, wherein the amount of the catalyst is adjusted so that a molar ratio of the catalyst to lactic acid is in the range of 0.1 to 10 mol %.

8. The method of claim 1, wherein the second organic solvent is selected from the group consisting of ethyl acetate, ether, methylene chloride, chloroform, and hexane.

9. The method of claim 1, wherein the amount of the second organic solvent is adjusted so that a weight ratio of water/second organic solvent in the range of 0.1 to 0.9.

* * * * *